(12) United States Patent
Massey et al.

(10) Patent No.: US 9,095,135 B2
(45) Date of Patent: Aug. 4, 2015

(54) MICROENCAPSULATED VOLATILE INSECT REPELLENT AND/OR INSECTICIDE AGENT AND METHODS OF MAKING AND USING THE SAME

(71) Applicants: Troy S. Massey, Rock Hill, SC (US); Jeffrey T. Langley, Rock Hill, SC (US)

(72) Inventors: Troy S. Massey, Rock Hill, SC (US); Jeffrey T. Langley, Rock Hill, SC (US)

(73) Assignee: Fashion Chemicals, GmbH & Co. KG, Geretsried (DE)

( * ) Notice: Subject to any disclaimer, the term of this patent is extended or adjusted under 35 U.S.C. 154(b) by 0 days.

(21) Appl. No.: 13/741,174

(22) Filed: Jan. 14, 2013

(65) Prior Publication Data
US 2013/0185817 A1    Jul. 18, 2013

Related U.S. Application Data

(60) Provisional application No. 61/585,905, filed on Jan. 12, 2012.

(51) Int. Cl.
*A01N 25/28* (2006.01)
*A01N 37/02* (2006.01)

(52) U.S. Cl.
CPC .............. *A01N 25/28* (2013.01); *A01N 37/02* (2013.01); *Y10T 428/2985* (2015.01); *Y10T 428/2989* (2015.01)

(58) Field of Classification Search
None
See application file for complete search history.

(56) References Cited

U.S. PATENT DOCUMENTS

| | | | |
|---|---|---|---|
| 5,587,401 A * | 12/1996 | Vander Meer et al. | 514/675 |
| 6,113,935 A * | 9/2000 | Rodson et al. | 424/408 |
| 6,306,415 B1 | 10/2001 | Reifenrath | |
| 6,444,216 B2 | 9/2002 | Reifenrath | |
| 6,703,127 B2 | 3/2004 | Davis et al. | |
| 6,835,334 B2 | 12/2004 | Davis et al. | |
| 6,953,814 B2 | 10/2005 | Reifenrath | |
| 7,241,497 B2 | 7/2007 | Magill et al. | |
| 7,244,497 B2 | 7/2007 | Hartmann et al. | |
| 7,470,738 B2 * | 12/2008 | Sumiya et al. | 524/356 |
| 7,550,200 B2 | 6/2009 | Hart et al. | |
| 7,579,078 B2 | 8/2009 | Hartmann et al. | |
| 7,790,283 B2 | 9/2010 | Hartmann et al. | |
| 7,938,897 B2 | 5/2011 | Hart et al. | |
| 8,173,257 B2 | 5/2012 | Hartmann et al. | |
| 8,753,676 B2 | 6/2014 | Kritzman et al. | |
| 2005/0267210 A1 | 12/2005 | Reifenrath | |
| 2006/0257441 A1 * | 11/2006 | Komai et al. | 424/405 |
| 2007/0243223 A1 | 10/2007 | Alasri et al. | |
| 2009/0053271 A1 | 2/2009 | Giner et al. | |
| 2011/0015072 A1 | 1/2011 | Hechavarria et al. | |
| 2012/0129694 A1 | 5/2012 | Ditmarsen et al. | |
| 2012/0136056 A1 | 5/2012 | Reifenrath | |

FOREIGN PATENT DOCUMENTS

| | | |
|---|---|---|
| EP | 1840145 | 10/2007 |
| EP | 2589290 | 5/2013 |

OTHER PUBLICATIONS

International Search Report and Written Opinion for International (PCT) Patent Application No. PCT/IB2014/000203, mailed Jun. 12, 2014, 10 pages.

* cited by examiner

*Primary Examiner* — Michael B Pallay
(74) *Attorney, Agent, or Firm* — Sheridan Ross P.C.

(57) ABSTRACT

The disclosure is capsules containing an active arthropod agent and to methods of making and using the same. The active arthropod agent can be a fatty acid having six or more carbon atoms. The capsules have a polymeric wall that controls the release of the active arthropod agent. The active agent can repellent, impair and/or kill insects.

23 Claims, 9 Drawing Sheets

MICROENCAPSULATED VOLATILE INSECT REPELLENT AND/OR INSECTICIDE AGENT AND METHODS OF MAKING AND USING THE SAME

CROSS REFERENCE TO RELATED APPLICATIONS

The present application claims the benefits of U.S. Provisional Application Ser. No. 61/585,905 filed Jan. 12, 2012 entitled "MICROENCAPSULATION OF VOLATILE INSECT REPELLENT AND INSECTICIDE AGENTS", the entire contents of which is incorporated herein by this reference.

FIELD OF INVENTION

This disclosure is directed to arthropodal compositions in the form of capsules containing an active arthropod agent, more particularly to capsules containing an active arthropod agent and methods of making and using the same.

BACKGROUND OF THE INVENTION

Arthropods can present be a health hazard to mammals, including humans, crops and food supplies. Additionally, arthropods can cause economic damage, particularly to the ecosystem. For example, arthropods can spread diseases, damage crops and food supplies.

Arthropods can bite and sting. Their bites and/or stinks can be painful and, in some instances, can be life threatening. They can also damage crops, forests and food supplies. In the case of food supplies, arthropods can consume and/or contaminant the food.

Effective compositions for managing arthropod populations are needed. Particularly compositions that are substantially environmentally benign, economical, and effective over extended periods of time.

SUMMARY OF THE INVENTION

These and other needs are addressed by the various embodiments and configurations of the present disclosure.

In accordance with some embodiments is a composition having a wall defining a void volume and an active arthropod agent filing at least some of the void volume. Preferably, the active arthropod agent fills at least most of the void volume, more preferably more than about 90% of the void volume. The wall is permeable and controls the release of the active arthropod agent. The wall is preferably a polymeric material. The polymeric material of the wall is one of a polyurethane, polyurea, urea-formaldehyde, urea-resorcinol-formaldehyde, melamine formaldehyde or combination thereof. The wall is preferably a melamine formaldehyde resin. Commonly, the active arthropod agent has a calculated vapor pressure at 25 degrees Celsius of more than about $1\times10^{-6}$ mm Hg. The arthropodal composition is preferably in the form of capsules. Typically, the capsules have an average capsule size of no more than about 1,000 µm. The average capsule size is preferably from about 1 to about 100 µm. Typically, the active arthropod agent is a fatty acid having six or more carbon atoms or a mixture of fatty acids having six or more carbon atoms. More typically, the active arthropod agent contains one or more of a $C_6$ fatty acid, $C_7$ fatty acid, $C_8$ fatty acid, $C_9$ fatty acid, $C_{10}$ fatty acid, $C_{11}$ fatty acid, and $C_{12}$ fatty acid. Preferably, the active arthropod agent contains one or more of a $C_8$ fatty acid, $C_9$ fatty acid, and $C_{10}$ fatty acid. The active arthropod agent can include one or more solvents and/or diluents.

In accordance with some embodiments is a device having a target substrate and one or more capsules positioned one or both of on and in the target substrate. The target substrate is preferably one or more of a hard surface, polymeric coating, polymeric film, botanical organism, foodstuff, and/or film, textile, and an animal. The one or more capsules have a wall defining a void volume and an active arthropod agent filing some of the void volume, preferably filling at least most of the void volume. The active arthropod agent preferably has a calculated vapor pressure at 25 degrees Celsius of more than about $1\times10^{-6}$ mm Hg. The wall is permeable and controls the release of active arthropod agent. The wall is preferably a polymeric material. The polymeric material of the wall is one of a polyurethane, polyurea, urea-formaldehyde, urea-resorcinol-formaldehyde, melamine formaldehyde or combination thereof. The capsules have an average capsule size. The average capsule size is preferably no more than about 1,000 µm. More preferably, the capsules have an average capsule size from about 1 to about 100 µm. Generally, the active arthropod agent is a fatty acid having six or more carbon atoms or a mixture of fatty acids having six or more carbon atoms. More generally, the active arthropod agent contains one or more of a $C_6$ fatty acid, $C_7$ fatty acid, $C_8$ fatty acid, $C_9$ fatty acid, $C_{10}$ fatty acid, $C_{11}$ fatty acid, and $C_{12}$ fatty acid. Preferably, the active arthropod agent contains one or more of a $C_8$ fatty acid, $C_9$ fatty acid, and $C_{10}$ fatty acid. The active arthropod agent can include one or more solvents and/or diluents.

In some instances, the device includes discrete gel droplets of a cross-linked gel containing a gelling agent and a cross-linking agent. The discrete gel droplets are preferably in the form of one of a continuous or discontinuous film. The discrete gel droplets interconnect the capsules to the target substrate. The gelling agent is preferably one of a polysaccharide, nonionic polymer, inorganic polymer, polyanion, polycation, alginate, natural ionic polysaccharide, chitosan, gellan gum, xanthan gum, hyaluronic acid, heparin, pectin, carrageenan polyacrylic acid, polymethacrylic acid, a polyethylene imine, polylysine, polyvinyl alcohol, sodium silicates, and mixtures thereof. The cross-linking agent is preferably a multivalent ion. The multivalent ion is one of magnesium, calcium, zinc, barium, strontium, aluminum, iron, manganese, nickel, cobalt, copper, cadmium, lead, or mixtures thereof.

In accordance with some embodiments is a system containing one or more capsules, each of the capsules have a wall defining a void volume, an active arthropod agent filling some of the void volume and an average capsule size. Preferably, at least most of the void volume is filled with the active arthropod agent. The average capsule size is no more than about 1,000 μm. Preferably, the average capsule size is from about 1 to about 100 μm. In some configurations, the system further includes a target substrate. The target substrate is one or more of a hard surface, polymeric coating, polymeric film, botanical organism, foodstuff, textile, and an animal. The one or more capsules are preferably positioned one or both of on or in the target substrate. In some configurations, the system further includes discrete gel droplets of a cross-linked gel. The cross-linked gel contains a gelling agent and a cross-linking agent. The discrete gel droplets preferably interconnect the one or more capsules to the target substrate and are in the form of one of a continuous or discontinuous film.

The wall is a polymeric material that controls one or both of release rate and period of efficacy of the active arthropod agent. The polymeric material can be permeable and/or can control one or both of the rate of release of the active arthropod agent into the environment and the period of efficacy of the active arthropod agent. Preferably, the polymeric material is one of a polyurethane, polyurea, urea-formaldehyde, urea-resorcinol-formaldehyde, melamine formaldehyde or combination thereof. The wall decreases the rate of release of the active arthropod agent into the environment. Compared to the active arthropod agent in non-encapsulate form, the rate of release of the active arthropod agent by the capsule wall is about 90% or less than that of the non-encapsulated active arthropod agent. The wall increases the period of efficacy of the active arthropod agent. Compared to the active arthropod agent in non-encapsulate form, the period of efficacy of the encapsulated active arthropod agent is about 110% or more than that of the non-encapsulated active arthropod agent.

The gelling agent is one of a polysaccharide, nonionic polymer, inorganic polymer, polyanion, polycation, alginate, natural ionic polysaccharide, chitosan, gellan gum, xanthan gum, hyaluronic acid, heparin, pectin, carrageenan polyacrylic acid, polymethacrylic acid, a polyethylene imine, polylysine, polyvinyl alcohol, sodium silicates, and mixtures thereof. The cross-linking agent is one of magnesium, calcium, zinc, barium, strontium, aluminum, iron, manganese, nickel, cobalt, copper, cadmium, lead, or mixtures thereof.

The active arthropod agent has a calculated vapor pressure at 25 degrees Celsius of more than about $1 \times 10^{-6}$ mm Hg. Commonly, the active arthropod agent is a fatty acid having six or more carbon atoms or a mixture of fatty acids having six or more carbon atoms. More commonly, the active arthropod agent contains one or more of a $C_6$ fatty acid, $C_7$ fatty acid, $C_8$ fatty acid, $C_9$ fatty acid, $C_{10}$ fatty acid, $C_{11}$ fatty acid, and $C_{12}$ fatty acid. Preferably, the active arthropod agent contains one or more of a $C_8$ fatty acid, $C_9$ fatty acid, and $C_{10}$ fatty acid. The active arthropod agent can include one or more solvents and/or diluents.

In some instances, the system further includes an arthropod. The arthropod is one or more of repelled, impaired, incapacitated or killed by the active arthropod agent released into the environment by the capsule.

"Capsule" generally refers a closed-walled container having an interior void. The capsule may have any shape. The capsule typically has a shape resembling one of sphere or ellipsoid. Typically, the ellipsoid has a shape generally resembling one of a scalene, oblate or prolate ellipsoid. Furthermore, the capsule may or may not have one or more planes of symmetry. The term capsule can refer to a microcapsule, macrocapsule and a mixture of microcapsules and macrocapsules.

"Active arthropod agent" generally refers to composition that repels, impairs, incapacitates, and/or kills an arthropod. The active arthropod agent may comprise a chemical compound or a mixture of chemical compounds. When the active arthropod agent comprises a mixture of chemical compounds, one or more of the chemical compounds comprising the active arthropod agent repels, impairs, incapacitates, or kills an arthropod. "Repels" generally refers to the active arthropod agent driving and/or forcing an arthropod back and/or away from the active arthropod agent and/or device, apparatus, system or composition containing the active arthropod agent. "Impairs" generally refers to an active arthropod agent and/or device, apparatus, system or composition containing the active arthropod agent weakening and/or damaging an arthropod. "Incapacitates" generally refers to an arthropod functioning in an abnormal manner after being exposed to the active arthropod agent and/or device, apparatus, system or composition containing the active arthropod agent. "Kills" generally refers to an active arthropod agent and/or device, apparatus, system or composition containing the active arthropod agent being the cause of death of an arthropod. The active arthropod agent can include one or more solvents and/or diluents. The diluent and/or solvent may be one of an organic material, inorganic material or mixture thereof. The organic material may be one of alkane, alkene, ether, ester, alcohol, aldehyde, or combination thereof. The organic material may be linear, branched, acyclic, cyclic, non-aromatic or aromatic. The inorganic material may be silicone or such.

"Arthropod" generally includes spiders, sea spiders, scorpions, centipedes, millipedes, pauropoda, symphyla, insects and entognatha.

These and other advantages will be apparent from the disclosure contained herein.

As used herein, the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The preceding is a simplified summary of the disclosure to provide an understanding of some aspects disclosed herein. This summary is neither an extensive nor exhaustive overview of the disclosure and its various embodiments. It is intended neither to identify key or critical elements nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate examples of the composition and how the composition can be made and used and are not to be construed as limiting the disclosure to only the illustrated and described examples.

Further features and advantages will become apparent from the following, more detailed, description of the disclosure as illustrated by the drawings referenced below.

FIG. 6A shows Argentine ants killed the composition and FIG. 6B shows a close-up view of Argentine ants killed by the composition;

DETAILED DESCRIPTION OF THE INVENTION

Figures 1A, 1B:
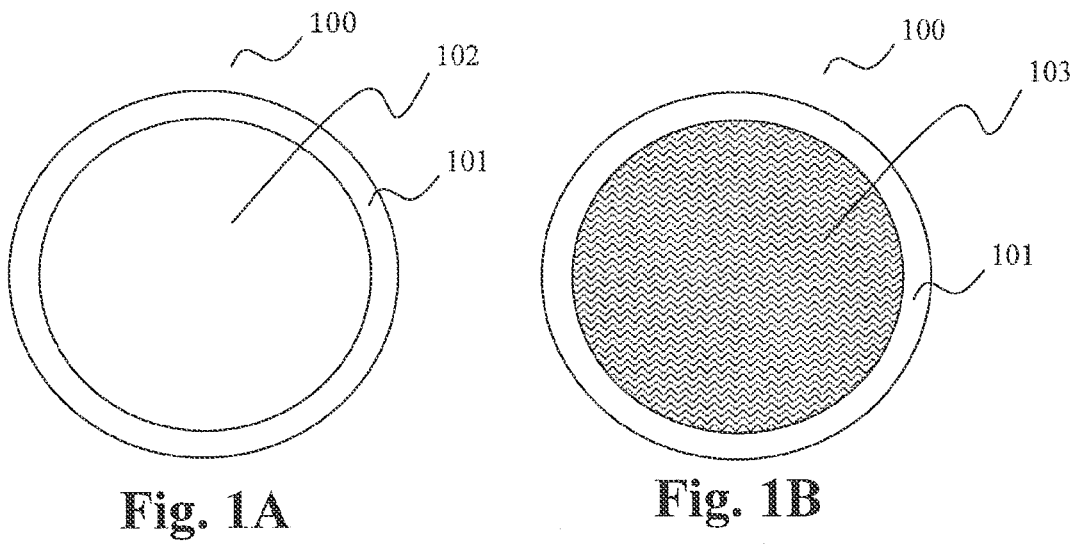
FIGS. 1A and 1B depict cross-sectional views of compositions as disclosed herein.

These and other needs are met by the present disclosure. This disclosure is generally directed to compositions comprising capsules containing one or more active arthropod agents. Capsule 100 comprises a wall 101 and a void volume 102 (FIG. 1A). The wall 101 comprises a wall material. The active arthropod agent 103 substantially fills some of the void volume 102 (FIGS. 1A and 1B), preferably at least most of the void volume. Capsule 100 may comprise a microcapsule, macrocapsule or a mixture micro- and macro-capsules. In accordance with some embodiments, a plurality of microcapsules may agglomerate and/or aggregate to form macrocapsules.

Commonly, the active arthropod agent 103 fills most of the void volume 102 (FIG. 1B). More commonly, the active arthropod agent 103 fills more than about 60%, even more commonly fills more than about 70%, yet even more commonly fills more than about 80%, still yet even more commonly fills more than about 85%, still yet even more commonly fills more than about 90%, still yet even more commonly fills more than about 95%, still yet even more commonly about fills more than about 98%, still yet even more commonly fills more than about 99% or yet still even more commonly fills about 100% of the void volume 102.

The active arthropod agent can be any agent that repels, impairs, incapacitates, or kills an arthropod. The active arthropod agent may comprise a chemical compound or a mixture of chemical compounds. When the active arthropod agent comprises a mixture of chemical compounds, one or more of the chemical compounds may repel, impair, incapacitate, or kill an arthropod.

The active arthropod agent is commonly an organic compound or mixture of organic compounds having a substantially high vapor pressure. Commonly, the active arthropod agent comprises an organic compound or mixture of organic compounds having a calculated vapor pressure at about 25 degrees Celsius of more than about 1×10 mm Hg. More commonly, the active arthropod agent has a calculated vapor pressure at about 25 degrees Celsius of from about 0.1 to about $5.0 \times 10^{-5}$ mm Hg. The vapor pressure of the active arthropod agent may be calculated by any method known in the art and/or measured by any standard analytical method know within the art. Non-limiting examples of two standard vapor pressure calculation methods are ACD Labs' ACD/PhysChem Suite and the United States Environmental Protection Agency's EIP Suite™.

The active arthropod agent can include one or more solvents and/or diluents. The diluent and/or solvent may be one of an organic material, inorganic material or mixture thereof. The organic material may be one of alkane, alkene, ether, ester, alcohol, aldehyde, mineral oil, or combination thereof. The organic material may be linear, branched, acyclic, cyclic, non-aromatic or aromatic. Examples of organic materials include without limitation hexanes, pentanes, benzenes, toluenes, pyridines, ethyl acetate, diethyl ether, methanol, ethanol, isopropanol, acetone, methylene chloride, chloroform, and mixtures thereof. Mineral oil includes without limitation, mineral oils comprising alkanes, cyclic paraffins, $C_{15-40}$ alkanes, natural and synthetic oils such as triglycerides, plant and animal oils, oils and esters of mono and polyhydic alcohols, and mixtures thereof. The inorganic material may be silicone oil. In some formulations, the active arthropod agent is commonly free of one or both of an emulsifier and a solvent and/or diluent. Commonly, the active arthropod agent comprises 0 wt % of one or more of an emulsifier, solvent and/or diluent. More commonly, the arthropod agent comprises about 5 wt % of one or more of an emulsifier, solvent and/or diluent, even more commonly about 10 wt %, yet even more commonly about 20 wt %, still yet even more commonly about 30 wt %, still yet even more commonly about 40 wt %, still yet even more commonly about 50 wt %, still yet even more commonly about 60 wt %, still yet even more commonly about 70 wt %, still yet even more commonly about 80 wt %, or yet still even more commonly about 90 wt % of one or more of an emulsifier, solvent and/or diluent. Generally, the arthropod agent comprises about 5 wt % of one or more of an emulsifier, solvent and/or diluent, more generally about 10 wt %, even more generally about 20 wt %, yet even more generally about 30 wt %, still yet even more generally about 40 wt %, still yet even more generally about 50 wt %, still yet even more generally about 60 wt %, still yet even more generally about 70 wt %, still yet even more generally about 80 wt %, or yet still even more generally about 90 wt % of one or more of an emulsifier, solvent and/or diluent, the remainder being one or more fatty acids.

The active arthropod agent is typically unsupported. That is, the active arthropod agent is typically not supported on one or more of clays, aluminates, silicates, and hydrated aluminum silicates.

Typically, the active arthropod agent is a fatty acid or a mixture of fatty acids. The fatty acid may be branched, non-branched, or a mixture of branched and non-branched fatty acids. The fatty acid may be saturated, unsaturated, or a mixture of saturated and unsaturated fatty acids. In some formulations, the active arthropod agent commonly comprises unsaturated, non-branched fatty acids. In some formulations, the active arthropod agent may comprise branched fatty acids, the branched fatty acids may be saturated, unsaturated or a mixture of saturated and unsaturated branched fatty acids. The active arthropod agent typically comprises a fatty acid having six or more carbon atoms. More typically, the arthropod agent comprises a mixture of fatty acids, each of which comprises fatty acids having six or more carbon atoms. As taught in U.S. Pat. No. 6,306,415 the active arthropod agent can be a fatty alcohol, fatty ketone, fatty aldehyde, fatty lactone, or mixture thereof.

In some formulations, the active arthropod agent may comprise saturated, non-branched fatty acids. The active arthropod agent may be one or more of a $C_6$ fatty acid, $C_7$ fatty acid, a $C_8$ fatty acid, $C_9$ fatty acid, $C_{10}$ fatty acid, $C_{11}$ fatty acid, $C_{12}$ fatty acid, or a mixture thereof. The active arthropod agent may be one or more of heaxanoic acid, heptanoic acid, octanoic acid, nonanoic acid, decanoic acid, undecanoic acid, dodecanoic acid, or a mixture thereof. Commonly, the active arthropod agent comprises one or more of octanoic acid, nonanoic acid and decanoic acid. More commonly, the active arthropod agent comprises a mixture of octanoic acid, nonanoic acid, and decanoic acids.

The $C_8$, $C_9$, and $C_{10}$ fatty acids can be present at any molar and/or weight ratio. Typically, the $C_8$, $C_9$, and $C_{10}$ fatty acids are present at about a 1:1:1 molar and/or weight ratio. More typically, the one of $C_8$, $C_9$, and $C_{10}$ fatty acids is present at one of molar and/or weight ratio of about 0.01:1, 0.05:1, 0.1:1, 0.5:1, 1.1:1, 1.5:1, 2:1, 5:1, 10:1, 50:1 or 100:1 to one or both of the other fatty acids. Even more typically, two or more of the $C_8$, $C_9$, or $C_{10}$ are separately and independently preset at one of molar and/or weight ratio of 0.01:1, 0.05:1, 0.1:1, 0.5:1, 1.1:1, 1.5:1, 2:1, 5:1, 10:1, 50:1 or 100:1 to the other fatty acid. It can be appreciated that these ratios of fatty acids similarly apply to active arthropod agents comprising fatty alcohols, fatty ketones, fatty aldehydes, fatty lactones, or to mixtures thereof.

The wall material typically comprises a polymeric material, preferably an organic polymeric material. The polymeric material may be a thermoplastic material, a thermoset material or a combination and/or mixture thereof. In some formulations, the wall material is thermoplastic material. In some formulations, the wall material is a thermoset material. In some formulations, the wall material is a thermoset material having thermoplastic properties (such as, but not limited to an A-staged or B-staged thermoset material). Preferably, the wall material is selected from the group consisting of homopolymers and copolymers of polyolefins, polystyrenes, polyvinyls, polyacrylics, polyhalo-olefins, polydienes, polyoxides, polyesthers, polyacetals, polysulfides, polyesters, polythioesters, polyamides, polythioamides, polyurethanes, polythiourethanes, polyureas, polythioureas, polyimides, polythioimides, polyanhydrides, polythianhydrides, polycarbonates, polythiocarbonates, polyimines, polysiloxanes, polysilanes, polyphosphazenes, polyketones, polythioketones, polysulfones, polysulfoxides, polysulfonates, polysulfoamides, polyphylenes, and mixtures thereof.

The polymeric material may or may not be permeable to the active arthropod agent. Commonly, the polymeric material is permeable to the active arthropod agent. More commonly, the polymeric material is permeable to the active arthropod agent. Preferably, the polymeric material having permeable properties to the active arthropod agents releases at a sufficient rate enough of the active arthropod agent to one or more of repel, impair, incapacitate or kill an arthropod. Generally, the release rate of the active arthropod agent by the polymeric material is at about 32 degrees Celsius from about 0.02 to about 19 µg/cm²-h, more generally from about 0.05 to about 18 µg/cm²-h, or even more generally from about 0.1 to about 17 µg/cm²-h. Some formulations, the release rate of the active arthropod agent by the polymeric material at about 32 degrees Celsius is typically more than about 22 µg/cm²-h.

Active arthropod agents having a vapor pressure at about 25 degrees Celsius of more than about $1 \times 10^{-6}$ mm Hg are commonly more rapidly released into the surrounding environment than active arthropod agents having a vapor pressure of less than about $1 \times 10^{-6}$ mm Hg. Generally, the arthropod active agent or at least one of the arthropod active agents comprising a mixture of arthropod active agents has a vapor pressure at 125 degrees Celsius between about 0.1 mm Hg and about 10 mm Hg. More generally, the arthropod active agent or at least one of the arthropod active agents comprising a mixture of arthropod active agents has a vapor pressure at 125 degrees Celsius between about 5 mm Hg and about 100 mm Hg. In some formulations, the arthropod active agent at least first and second arthropod active agents, the first arthropod active agent having a first arthropod active agent vapor pressure at 125 degrees Celsius between about 0.1 mm Hg and about 10 mm Hg and the second arthropod active agent having has a second arthropod active agent vapor pressure at 125 degrees Celsius between about 5 mm Hg and about 100 mm Hg. The rate of release of the active arthropod agent can effect the period of efficacy of the active arthropod agent. For example, having too little of the active arthropod agent released into the surrounding environment can reduce the effectiveness of the active arthropod agent to repel, impair, incapacitate or kill an arthropod. However, having too much of the active arthropod agent released to the surrounding environment can waste the active arthropod agent by overdosing. Furthermore, overdosing typically reduces the period of efficacy of the active arthropod agent.

Supporting the active arthropod agent typically does not substantially reduce the rate of release of the active arthropod agent into the atmosphere nor does it substantially increase the period of efficacy. However, encapsulation of the active arthropod agent 103 can modulate the rate of release and/or period of efficacy of the active arthropod agent 103. That is, the wall 102 of the capsule can substantially control the rate release of the active arthropod agent 103 into the surrounding environment compared to non-capsulated active arthropod agent 103. Moreover, the wall 102 of capsule 100 can substantially extend the temporal period over which the active arthropod agent 103 is released to the environment. Typically, extending the temporal period over which the active arthropod agent 103 is released to the environment can extend the period of efficacy of the active arthropod agent 103 to one or more of repel, impair, incapacitate or kill arthropods.

The wall 102 can substantially decrease the rate of release of the active arthropod agent 103 into the surrounding environment. Commonly, the wall 102 decreases the rate of release of the active arthropod agent into the environment. For example, compared to the active arthropod agent alone, the rate of release of the active arthropod 103 agent by the wall 102 of the capsule 100 is commonly 90% or less than that of the active arthropod agent alone, more commonly 80% or less, even more commonly 70% or less, yet even more commonly 60% or less, still yet even more commonly 50% or less, still yet even more commonly 40% or less, still yet even more commonly 30% or less, still yet even more commonly 20% or less, or yet still even more commonly 10% or less than that of the active arthropod agent alone (that is, the non-encapsulated active arthropod agent).

Furthermore, the wall 102 can substantially increase the period of efficacy of the active arthropod agent 103 compared to non-encapsulated active arthropod agent 103. The period of efficacy of the encapsulated active arthropod agent 103 is typically 110% or more, more typically 130% or more, even more typically 150% or more, yet even more typically 180% or more, still yet even more typically 200% or more, still yet even more typically 250% or more, still yet even more typically 300% or more, still yet even more typically 400% or more, or still yet even more typically 500% or more that of the non-encapsulated active arthropod agent 103.

Any of a variety of processes known in the art may be used to encapsulate the active arthropod agent 103. A typical method that may be used to encapsulate the active arthropod agent 103 is to disperse droplets of the active arthropod agent 103 in an aqueous solution. Commonly, the dispersed drops comprise the active arthropod agent 103 in a liquid form. While not wanting to limited by example, the dispersed droplets are formed substantially at about and/or above the melting point of the active arthropod agent 103.

Walls 102 are formed around the dispersed droplets using techniques such as coacervation, interfacial polymerization and in situ polymerization, all of which are known to those having ordinary skill in the arts of encapsulation and/or solution polymerization. One non-limiting example is the method for forming gelatin capsules by coacervation. Other non-limiting examples include the methods for forming polyurethane or polyurea capsules by interfacial polymerization, and urea-formaldehyde, urea-resorcinol-formaldehyde, and melamine formaldehyde capsules by in situ polymerization. In accordance with some embodiments, the wall material encapsulating the active arthropod agent 103 is a melamine-formaldehyde resin.

The capsules 100 generally have an average capsule size. The average capsule size typically depends on one or both of the active arthropod agent 103 and the application in which the encapsulated active arthropod agent is to be used. Application of use commonly refers to the device or system the capsules 100 are to be used in and/or the antropod to be treated. Typically, the capsules 100 have an average capsule size of no more than about 1,000 μm. More typically, the capsules 100 have an average capsule size from about 1 to about 100 μm, even more typically from about 2 to about 50 μm, or yet even more typically from about 3 to about 40 μm.

The capsules 100 may be microcapsules, macrocapsules or a mixture and/or combination of micro- and macro-capsules. Microcapsules generally have an average capsule size of no more than about 100 μm. More generally, microcapsules have an average size from about 1 to about 100 μm, even more generally from about 2 to about 50 μm, or yet even more generally from about 3 to about 40 μm. Macrocapsule may refer to single capsule or to an agglomeration of capsules. Macrocapsules typically have an average capsule size of about 100 μm or more. More typically, macrocapsules have an average size from about 100 to about 10,000 μm or more typically from about 500 to about 5,000 μm.

The capsules 100 may be applied to a target substrate. The target substrate may be a fluid, hard surface, polymeric coating, polymeric film, botanical organism, foodstuff, textile, or an animal. The fluid may be one of gas or liquid. Preferably, the gas is air and the fluid comprises water, such as pond, stream or lake. The hard surface may be a cellulosic material (non-limiting examples include: wood, straw, hay, and so forth), mineral material (non-limiting examples include: marble, onyx, slate, and so forth), metallic material (non-limiting examples include: stainless steel, copper, steel, iron and so forth), ceramic, glass, polymeric material (non-limiting examples include naturally derived polymeric materials, man-made polymeric materials, organic polymeric materials, inorganic polymeric materials, homopolymers, copolymers and so forth), and leather (non-limiting examples include leather derived from bovine, swine, ostrich, buffalo, sheep, snake, and so forth). The polymeric coating and/or film can be any polymeric material formulated as a coating, such as paint, varnish, other protective coating. The botanical organism can be a crop plant, ornamental plant, lawn, grass, seed, flower, tree, fruit, vegetable or other botanical. The foodstuff can be any feed grain (such as but not limited to wheat, corn, bran, etc.), animal/livestock feed material, fruit, vegetable, legume, or packing or storage container therefor. The textile material may be a man-make (such as without limitation a synthetic polymer, as for example nylon, elastane, polyester, polytetrafluoroethylene, and so forth) or naturally derived textile material (such as without limitation cotton, silk, wool, rayon, and so forth). The textile material may be an item of apparel (such as without limitation: a blouse, shirt, jacket, coat, dress, skirt, pants, socks, hat, or so forth), a household item (such as without limitation: a rug, upholstery, drape, curtain, bedding, and so forth), other textile items (such as without limitation textile items utilized in: camp equipment, automotive, aeronautical, watercraft, sporting equipment, farming and horticultural equipment and building decorative items and so forth). The animal may be a human, a companion, and/or an animal raised for profit (such as, livestock). In some applications, the target substrate includes bed nets, premises, livestock or stored grain.

In some configurations, the capsules 100 may be incorporated in the target substrate. For example, the capsules 100 may be incorporated in the substrate by forming a continuous and/or discontinuous matrix of capsules in the target substrate. Furthermore, the capsules 100 may be incorporated on the substrate by forming a continuous and/or discontinuous film of capsules on the target substrate. Moreover, the continuous or discontinuous film of capsules may be formed on the fibers comprising a textile material.

Figure 2:
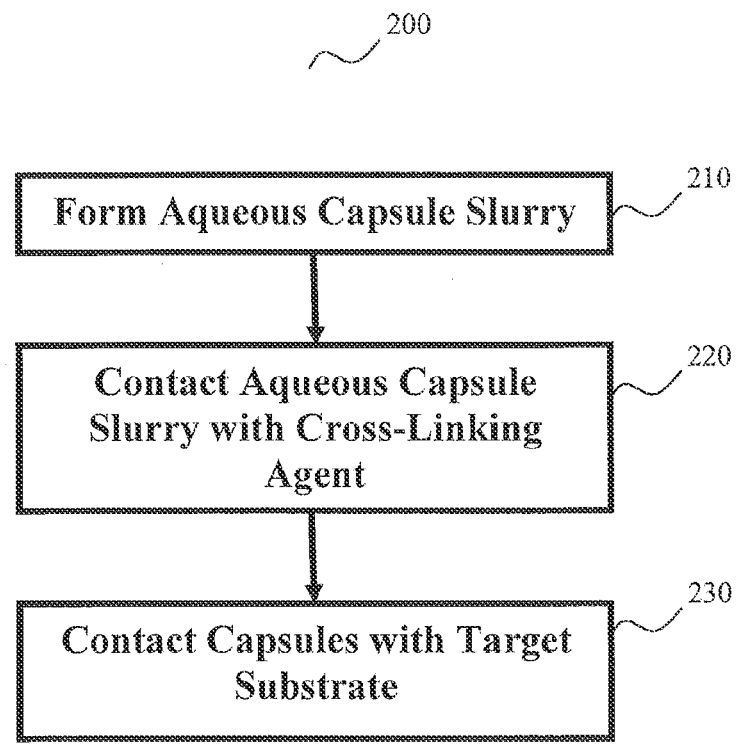
FIG. 2 depicts a process of making the composition of FIG. 1 as disclosed herein.

FIG. 2 depicts a process 200 for applying capsules 100 containing the active arthropod agent 103 to a target substrate. In step 210, capsules 100 containing the active arthropod agent 103 are slurried with a gelling agent to form aqueous capsule slurry 110. The gelling agent is typically provided at a concentration in the aqueous solution to sufficiently coat the capsules with a viscous coating of the gelling agent.

Gelling agents include without limitation polysaccharides, nonionic polymers, inorganic polymers, polyanions and polycations. Non-limiting examples of polysaccharides include alginate and natural ionic polysaccharides such as chitosan, gellan gum, xanthan gum, hyaluronic acid, heparin, pectin and carrageenan. Examples of ionically crosslinkable polyanions include, but are not limited to, polyacrylic acid, and polymethacrylic acid. Examples of crosslinkable polycations include without limitation polyethylene imine and polylysine. A specific example of a non-ionic polymer is polyvinylalcohol. Sodium silicates are examples of useful inorganic polymers.

In accordance with some embodiments, polysaccharide alginate can serve as a gelling agent. Non-limiting examples of suitable alginates are salts of alginic acid, such as but not limited to sodium alginate and potassium alginate and mixtures thereof. An example of a suitable commercial alginate is SOBALG-FD 120 (manufactured by Grindsted, Inc. and sold under the Tradename SOBALG-FD 120, which is believed to be a sodium alginate).

Sodium alginate gelling agents are typically provided as an aqueous solution having from about 1 wt % to about 15 wt % of the sodium alginate in the aqueous solution. Typically, from about 1 wt % to about 15 wt % of sodium alginate is sufficient to coat the capsules with a viscous coating of the sodium alginate gelling agent. However, it should be appreciated that from about 1 wt % to about 15 wt % of alginate is non-limiting, the amounts and/or concentration alginate and/or gelling agent in the aqueous capsule slurry 110 may be less than about 1 wt % in some configurations and greater than about 15 wt % in others.

In step 220, the aqueous capsule slurry is contacted with a crosslinking agent to form a cross-linked gel solution. The cross-linked gel solution can comprise an alginate, a reactive silicone, a cross-linked polyurethane, or a film forming polymer. The crosslinking agent may be in the form of one of: a crosslinking composition; an aqueous solution containing the crosslinking agent; or non-aqueous solution (such as, without limitation an alcoholic solution or a non-alcoholic liquid organic solution containing the cross-linking agent). The crosslinking agent typically comprises a material capable of crosslinking the gelling agent to form the cross-linked gel solution. Commonly, the crosslinking agent includes multivalent ions, in particular multivalent cations. Multivalent cations useful in crosslinking the gelling agent include magnesium, calcium, zinc, barium, strontium, aluminum, iron, manganese, nickel, cobalt, copper, cadmium, lead, or mixtures thereof. Calcium, barium, and strontium are useful in particular embodiments, with calcium being a particularly useful for crosslinking the gelling agent.

While not wanting to be bound by any theory, it is believed that discrete gel droplets are formed, in step 220, by the contacting of the cross-linkable gel solution and the aqueous capsule slurry. The discrete gel droplets are believed to comprise two or more capsules agglomerated and/or aggregated by the cross-linked gel.

In some configurations, the capsules 100 are contacted with the target substrate (step 230) before forming the cross-linkable gel solution, in step 220. That is, the aqueous capsule slurry is contacted with the target substrate prior to the contacting of the crosslinking agent with the aqueous capsule slurry. The discrete gel droplets are believed to form a continuous or discontinuous film of capsules on the target substrate.

While in some configurations, the capsules 100 are contacted with the target substrate (step 230) after forming the cross-linkable gel solution, in step 220. That is, the aqueous capsule slurry is contacted with the cross-linking agent before the capsules 100 are contacted with the target substrate. The discrete gel droplets can be contacted with the target substrate to form a continuous or discontinuous film of capsules on the target substrate. Or, the discrete gel droplets can be separated from the crosslinking solution, rinsed with water and dried to a consistency of less than 1% moisture. The resulting discrete gel droplets may be incorporated and/or formed into the target substrate.

EXAMPLES

Microcapsules were prepared in the form of an aqueous slurry concentrate. The microcapsules contained a mixture of $C_8$, $C_9$ and $C_{10}$ fatty acids and had melamine-formaldehyde resin capsule wall. The aqueous slurry concentrate contained about 35.6 wt % capsules. The microcapsules comprised about 25 wt % of the melamine-formaldehyde resin and about 75 wt % of the $C_8$, $C_9$ and $C_{10}$ fatty acid mixture. The aqueous slurry concentrate contained about 27.4 wt % arthropod actives (that is, the $C_8$, $C_9$ and $C_{10}$ fatty acid mixture).

The aqueous slurry concentrate was diluted with water at various levels and for laboratory testing as an insect repellent and insecticide against various arthropods. The arthropods tested were adult female *Aedes aegypti* mosquitoes, adult mixed gender houseflies (*Musca domestica*), adult male and female German cockroaches (*Blatella germanica*), and Argentine ants. The various dilution levels were: a 1/10 dilution of the aqueous slurry concentrate which corresponds to a surface dose of about 431 µg/cm² of the arthropod actives; a 1/100 dilution which corresponds to about 43.1 µg/cm² of the arthropod actives; a 1/200 dilution which corresponds to about 21.5 µg/cm² of the arthropod actives; a 1/500 dilution is 8.6 µg/cm² of the arthropod actives; and a 1/1000 dilution which corresponds to about 4.3 µg/cm² of the arthropod actives.

Insecticidal Assay

One millimeter of the aqueous dilution of the microcapsule concentrate (35.6 wt % capsule dispersion in water) was pipetted evenly onto a 9 cm diameter disk (63.6 cm² exposed surface area) of filter paper (WHATMAN™ No. 1) contained in a standard size disposable plastic Petri dish. The petri dish had a ¾" stoppered hole centered in its lid for introduction of insects into the petri dish.

As a positive control, a formulation containing 15 wt % of the $C_8$, $C_9$ and $C_{10}$ fatty acid mixture adsorbed onto kaolin was prepared and dispersed in water. Aqueous dilutions of this control dispersion were applied to the filter paper/Petri dish assembly in separate control experiments.

For each formulation level tested, fifteen adult female *Aedes aegypti* mosquitoes (6-10 days old) were introduced into the covered Petri dish plate and observed for incapacitation at about 5, 10, and 25 minutes post-application, and at 24 hours post-application for incapacitation and mortality.

The incapacitation and pesticidal activities against 15 female *Aedes aegypti* mosquitoes are presented in Table 1. Two replicates were conducted on different days, (denoted as days 1 and 2). One milliliter of the aqueous dilution was applied evenly to the filter paper and tests were conducted within five minutes of the application. Distilled water (D.W.) produced no incapacitation or mortality over 24 hours.

TABLE 1

| Dosage Level | Incapacitated at 10 min | Incapacitated at 25 min | Time to 100% Incapacitation | Incapacitated at 24 hr. | Mortality at 24 hr. |
| --- | --- | --- | --- | --- | --- |
| 1/10* | 100% | 100% | 5 min | 100% | 100% |
| 1/10** | 100% | 100% | 5 min | 100% | 100% |
| 1/100* | 100% | 100% | 5 min | 100% | 93% |
| 1/100** | 100% | 100% | 5 min | 100% | 100% |
| 1/200* | 31% | 100% | 13 min | 100% | 80% |
| 1/200** | 100% | 100% | 10 min | 93% | 93% |
| 1/500* | 0% | 27% | 28 min | 100% | 53% |
| 1/500** | 0% | 100% | 25 min | 80% | 80% |
| 1/1000* | 0% | 0% | 85 min | 19% | 19% |
| 1/1000** | 0% | 0% | 90 min | 0% | 0% |
| D.W.* | 0% | 0% | — | 0% | 0% |
| D.W.** | 0% | 0% | — | 0% | 0% |

*Day 1 and
**Day 2

Incapacitation and pesticidal activities against 15 houseflies (*Musca domestica*, mixed sex) from Benzon, Inc. colony are presented in Table 2. One milliliter of the aqueous dilution was applied evenly to the filter paper and tests were conducted within five minutes of the application. Distilled water (D.W.) produced only slight incapacitation or mortality over 24 hours.

TABLE 2

| Dilution | Incapacitated at 10 min | Incapacitated 25 min | Incapacitated at 24 hr | Mortality at 24 hr |
| --- | --- | --- | --- | --- |
| 1/10 | 100% | 100% | 100% | 87% |
| 1/100 | 60% | 100% | 53% | 13% |
| 1/200 | 7% | 60% | 33% | 27% |
| 1/500 | 0% | 0% | 7% | 7% |
| 1/1000 | 0% | 0% | 27% | 20% |
| D.W. | 0% | 0% | 13% | 13% |

Incapacitation and pesticidal activities against 15 houseflies (*Musca domestica*, mixed genders) from the USDA ARS Gainesville colony are presented in Table 3. One milliliter of the aqueous dilution was applied evenly to the filter paper and tests were conducted within five minutes of the application. Significant incapacitation and mortality was observed with the USDA colony flies for the distilled water (D.W.) control at 24 hours, thereby limiting the value of the 24 hour observations for the test formulation.

TABLE 3

| Dilution | Incapacitated at 10 min | Incapacitated at 25 min | Incapacitated at 24 hr | Mortality at 24 h. |
| --- | --- | --- | --- | --- |
| 1/10 | 100% | 100% | 100% | 20% |
| 1/100 | 0% | 80% | 7% | 0% |

TABLE 3-continued

| Dilution | Incapacitated at 10 min | Incapacitated at 25 min | Incapacitated at 24 hr | Mortality at 24 h. |
|---|---|---|---|---|
| 1/200 | 0% | 20% | 20% | 7% |
| 1/500 | 0% | 0% | 53% | 53% |
| 1/1000 | 0% | 0% | 60% | 40% |
| D.W. | 0% | 0% | 69% | 60% |

Incapacitation and pesticidal activities against 10 mixed-gender German cockroaches (*Blatella germanica*, from Benzon, Inc. colony) are presented in Table 4. Two replicates were conducted on different days, (denoted as days 1 and 2). One milliliter of the aqueous dilution was applied evenly to the filter paper and tests were conducted within five minutes of application. No incapacitation or mortality was observed with the distilled water (D.W.) control over the test period.

TABLE 4

| Dilution | Incapacitated at 0 min | Incapacitated at 25 min | Incapacitated at 24 hr | Mortality at 24 hr |
|---|---|---|---|---|
| 1/10* | 67% | 83% | 83% | 67% |
| 1/10** | 50% | 100% | 100% | 75% |
| D.W.* | 0% | 0% | 0% | 0% |
| D.W.** | 0% | 0% | 0% | 0 |

*Day 1 and **Day 2

Repellency Assay Using Free Choice Cages

A test formulation was applied to two non-adjacent squares (4"×4" felt pads) and the positive control was applied to the remaining two squares in an 8"×8" ventilated cage. A repellent dose for the $C_8$, $C_9$ and $C_{10}$ fatty acid mixture typically occurs in the range of from about 0.3 to about 1.0 $mg/cm^2$. Insects were introduced onto a control pad through a small hole in the side of the ventilated cage. The ventilated cage lid was sealed in place to prevent insect escape and the cage was not forced-ventilated. At various times following introduction, readings of insect distribution between the control and treatment pads were taken. Incapacitation, if any, was recorded over a two-hour period. Repellency is defined as a greater than 50% proportion of insects on control pads.

Table 5 presents the effect of the aqueous slurry concentrate on German cockroaches in a free choice cage. One milliliter of the aqueous slurry concentrate was applied to two nonadjacent quadrants and distilled water was applied to the other quadrants. The German cockroaches were not repelled by the aqueous slurry concentrate at any point in time and roamed freely over all quadrants.

TABLE 5

| Time After Roaches Introduction | Roaches Incapacitation |
|---|---|
| 45 min | 30% |
| 105 min | 30% |
| 150 min | 40% |
| 24 hours | 0% |

Table 6 presents the effect of a 1/10 dilution the aqueous slurry concentration on German cockroaches in a free choice cage. One milliliter of the 1/10 dilution of the aqueous slurry concentrate was applied to two nonadjacent quadrants and distilled water was applied to the other quadrants. During the first 10 minutes, roaches were repelled by the treatment. However, from about 15 to about 25 minutes after roach placement, roaches were no longer repelled by the 1/10 dilution treatment.

TABLE 6

| Time after roach introduction | Roaches Incapacitation |
|---|---|
| 25 minutes | 11% |
| 24 hours | 0% |

Table 7 presents the effect of the control, kaolin powder, on German cockroaches in a free choice cage. One gram of the control kaolin powder was applied to two nonadjacent quadrants and the remaining quadrants were untreated. Roaches roamed all quadrants at will.

TABLE 7

| Time After Roaches Introduction | Roaches Incapacitation |
|---|---|
| 8 min | 0% |
| 25 min | 0% |
| 52 min | 0% |
| 72 hours | 0% |

Mosquito Repellency Assay Using an Olfactometer

A Finsod-Spielman olfactometer was used to determine mosquito repellency after application of test formulation to the human forearm. Fifteen adult female *Aedes aegypti* mosquitoes were placed in the upper chamber of the olfactometer. A fan placed on top of the upper chamber caused air to flow from the bottom of the lower chamber to the upper chamber. During a two-minute pretest with no human present, the number of mosquitoes traveling from the upper to lower chamber was recorded. An untreated forearm was placed just under the lower chamber to attract mosquitoes, but not allow them to bite. The number of mosquitoes entering the lower chamber was recorded over a five-minute period. After clearing the olfactometer of mosquitoes, a fresh batch of fifteen mosquitoes was introduced into the upper chamber and the test sequence was repeated, this time with a formulation treated forearm under the lower chamber.

Table 8 presents the results of two replicate (on two different days) olfactometer repellency tests of a 1/10 dilution of aqueous slurry concentrate applied to the forearm at an actives dose of about 0.47 $mg/cm^2$. Approximately 15 female *Aedes aegypti* mosquitoes were initially placed in the upper chamber

TABLE 8

| Time | Untreated % Responders | Treated % Responders |
|---|---|---|
| 2 m pre-test* | 13% | 20% |
| 2 m pre-test** | 0% | 15% |
| 1 m test* | 21% | 0% |
| 1 m test** | 13% | 0% |
| 3 m test* | 50% | 17% |
| 3 m test** | 60% | 18% |
| 5 m test* | 71% | 33% |
| 5 m test** | 80% | 45% |

*Day 1 and **Day 2

Spray Tests

The aqueous dilution of test formulations was placed in a trigger style 32 oz. spray bottle (All Purpose Sprayer, ACE® Hardware). Insects were placed in an acrylic cylinder (3 inches diameter by 4 inches in length). One end of the cylinder was covered in cheesecloth secured with rubber bands. The other end of the cylinder was similarly covered with cheesecloth, and a three-quarter inch diameter hole cut in the center of the cheesecloth. Insects were introduced through this hole and a cotton ball served as a stopper for the hole. The tip of the spray bottle was positioned just inside the cylinder by pushing the cotton ball to one side. Insects received one or two direct sprays from the bottle. After the sprayer tip was removed, the cotton ball was repositioned to prevent insect escape. Insects were observed for various lengths of time and the number of insects incapacitated or killed was recorded. For certain tests with houseflies, the houseflies were released in a 10×10×10 foot room. Resting flies were sprayed directly with test formulation and the number knocked down to the floor was recorded.

Table 9 presents spray tests for housefly (USDA ARS Gainesville colony) knockdown or incapacitation with a 1/10 dilution of the aqueous slurry concentrate. A distilled water spray served as the control. A single pump from a trigger-type sprayer delivered a dispersion of about 1 milliliter of the 1/10 diluted solution to fifty houseflies in the acrylic cylinder.

TABLE 9

| Post Spray Time | Incapacitated Control Houseflies | Incapacitated Treated Houseflies |
|---|---|---|
| 30 sec | 0% | 100% |
| 25 min | 0% | 100% |
| 24 hr | 50% Dead | 100% Dead |

Table 10 presents spray tests for mosquito (*Aedes aegypti*, Benzon, Inc. colony) knockdown and incapacitation with a 1/10 dilution of the aqueous slurry concentrate. A distilled water spray served as the control. A single pump from a trigger-type sprayer delivered a dispersion of about 1 milliliter of the 1/10 diluted solution to fifteen mosquitoes in the acrylic cylinder.

TABLE 10

| Post Spray Time | Incapacitated Control Mosquitoes | Incapacitated Treated Mosquitoes |
|---|---|---|
| 30 sec | 0% | 100% |
| 60 min | 0% | 100% |
| 48 hr | 0% Dead | 100% dead |

Table 11 presents spray tests for mixed gender German cockroaches (*Blatella germanica*, Benzon, Inc. colony) knockdown and incapacitation with a 1/10 aqueous dilution of the aqueous slurry concentrate. A distilled water spray served as the control. A single pump from a trigger-type sprayer delivered a dispersion of about 1 milliliter of the 1/10 diluted solution to ten German cockroaches in the acrylic cylinder.

TABLE 11

| Post Spray Time | Incapacitated Control Cockroaches | Incapacitated Treated Cockroaches |
|---|---|---|
| 10 min | 0% | 80% |
| 25 min | 0% | 80% |
| Re-spray at 25 min | 0% | 100% |
| 24 h | 0% | Not Determined |
| 48 h | Not Determined | 100% males/20% females |

Table 12 presents spray tests for female German cockroach (*Blatella germanica*, Benzon, Inc. colony) knockdown and incapacitation with a 1/10 aqueous dilution of the aqueous slurry concentrate. A distilled water spray served as the control. A single pump from a trigger-type sprayer delivered a dispersion of about 1 milliliter of the 1/10 diluted solution to thirty-two female German cockroaches in the acrylic cylinder.

TABLE 12

| Post Spray Time | Incapacitated Control Female Cockroaches | Incapacitated Treated Female Cockroaches |
|---|---|---|
| 5 min | 0% | 100% |
| 10 min | 0% | 100% |
| 25 min | 0% | 100% |
| 24 hr | 0% | 41% dead |
| 48 hr | 0% | 31% dead |
| 3 days | 0% | 38% dead |
| 5 days | 0% | 44% dead |
| 7 days | 20% Dead | 81% dead |

Table 13 presents spray tests for mixed gender German cockroach (*Blatella germanica*, Benzon, Inc. colony) knockdown and incapacitation with a 1/10 aqueous dilution of the aqueous slurry concentrate. A distilled water spray served as the control. A single pump from a trigger-type sprayer delivered a dispersion of about 1 milliliter of the 1/10 diluted solution to twenty, ten male and ten female, German cockroaches in the acrylic cylinder.

TABLE 13

| Post Spray Time | Incapacitated Males | Incapacitated Females |
|---|---|---|
| 5 min | 0% | 0% |
| 10 min | 0% | 0% |
| 25 min/Before re-spray | 0% | 0% |
| 25 min/After re-spray | 100% | 100% |
| 40 min | 100% | 100% |
| 24 hr | 40% dead | 20% dead |

Table 14 presents spray tests for mixed gender German cockroaches (*Blatella germanica*, Benzon, Inc. colony) knockdown and incapacitation with a 1/10 aqueous dilution of the aqueous slurry concentrate. A distilled water spray served as control. Two pumps from a trigger-type sprayer were delivered to twenty, ten male and ten female, German cockroaches in the acrylic cylinder. Each of the pumps delivered a dispersion of about 1 milliliter of the 1/10 diluted solution to the German cockroaches.

TABLE 14

| Post Spray Time | Incapacitated Males | Incapacitated Females |
|---|---|---|
| 5 min | 80% | 30% |
| 10 min | 90% | 10% |
| 2 hr | 60% | 0% |
| 24 hr | 0% | 0% |

Table 15 presents room spray test with a 1/10 dilution of the aqueous slurry concentrate for mixed gender houseflies (*Musca domestica*) in a 10'×10'×10' room. A single pump from a trigger-type sprayer delivered about one milliliter of the dilute solution per resting fly. Downed flies were swept under the table.

TABLE 15

| Spray Time | Effect |
|---|---|
| At time of spray | Immediate knockdown |
| 1 hour post spray | Floor sweep gave 20 downed flies |

Mosquitoes

Mosquito incapacitation was observed at dilutions up to 1/1000 (Table 1), corresponding to an actives dosage of about 4.3 µg/cm². It took from about 85 to about 90 minutes for the effect to be observed. The majority of mosquitoes recovered from incapacitation at about 24 hours after being exposed to this dosage level. Little, if any, mortality was observed at the 1/1000 dilution level.

At a higher dosage level, such as at about the 1/100 dilution level, which corresponds to an arthropod dosage level of about 43.1 µg/cm², incapacitation was more immediately (at about 5 minutes after exposure), and mortality, as judged by lack of insect movement at 24 hours, was essentially complete. Under the same test conditions at an actives dosage level of about 4.7 µg/cm², gave about 100% incapacitation at about 25 minutes and 12.5% mortality at about 24 hours and 88% mortality at about 48 hours after exposure (Table 15). Furthermore, at about a dosage level of 47 µg/cm² mortality levels at about 24 hours after exposure are about 100% (Table 16).

TABLE 16

| Formulation | Surface dose (µg/cm²) | Time to 100% Incapacitation | Incapacitation at 24 h | Mortality at 24 h | Mortality at 48 h |
|---|---|---|---|---|---|
| Encapsulated | 4.3 | 85-90 min | 0-19% | 0-19% | No data |
| Kaolin (control) | 4.7 | 25 min | 100% | 12.5% | 88% |
| Encapsulated | 43 | 5 min | 100% | 93-100% | No data |
| Kaolin (Control) | 47 | ≤10 min | 100% | 100% | 100% |
| D.W. | 0 | — | 0% | 0% | 8% |

Comparison of encapsulated and supported (kaolin) arthropod actives ($C_8$, $C_9$ and $C_{10}$ fatty acids) against *Aedes aegypti* mosquitoes in the filter paper/Petri dish assay. Distilled water (D.W.) produced no incapacitation or mortality over 24 hours and essentially no mortality at 48 hours (one mosquito out of 15).

In the olfactometer tests (Table 8), the majority of mosquitoes (70-80%) responded or flew towards the untreated arm. While the arm treated with the encapsulated arthropod active agent showed a repellent effect, reducing the mosquito responders to about 35-45% at an hour (that is, 1 hour) after application. Similar tests with a dosage level of about 15% arthropod actives in silicone oil formulation gave nearly zero responders.

Figure 4A:
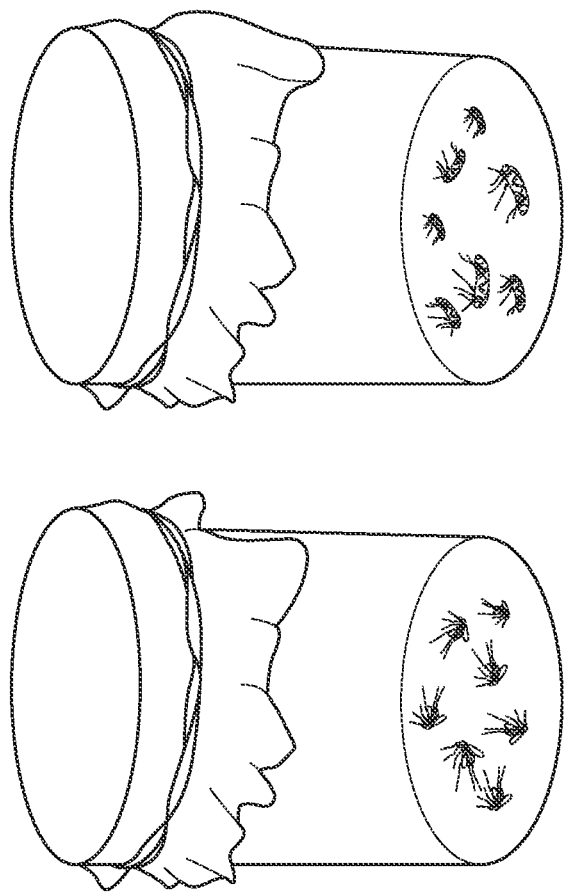
FIGS. 4A and 4B are photographs of results after mosquito and German cockroach cylinder sprays tests with a composition according to FIG. 1 with right hand side showing German cockroach knock down results and left hand side showing mosquito knocked down results.
Figure 4B:
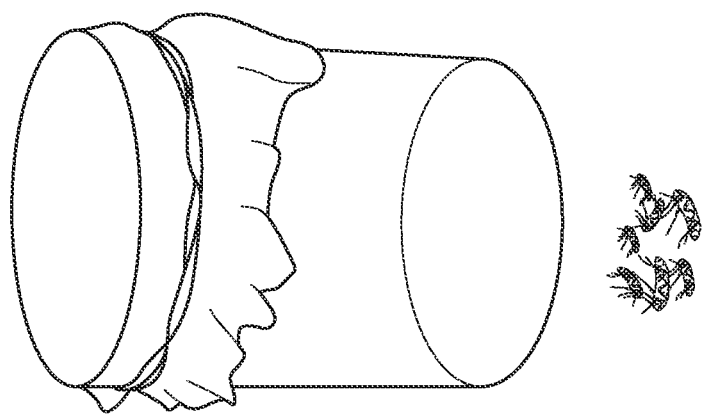
Figure 4B:
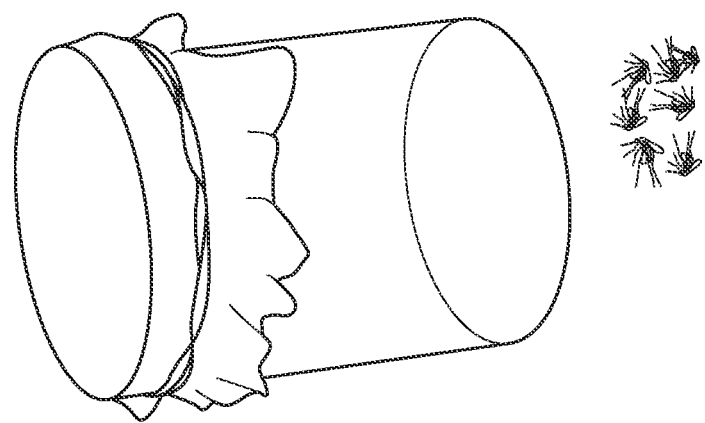

Cylinder spray tests of a 1/10 dilution formulation of the aqueous slurry concentrate (having about 2.7% arthropod actives) against mosquitoes (Table 10) was highly effective showing immediate and complete incapacitation at about 100%, and complete morality at about 100% at about 24 hour at exposure. FIGS. 4A and 4B show the mosquito cylinder spray tests (on the left hand side of the figures) with a 1/10 dilution of the aqueous slurry concentration with all of the mosquitoes knocked down.

Houseflies

Houseflies were more resistant than mosquitoes. Houseflies generally required a dosage level of about 431 µg/cm² (1/10 dilution, Table 2) to give 100% incapacitation at about 10 minutes and morality at about 24 hours after exposure. Similar results (about 100% incapacitation at 10 minutes after exposure and about 93% mortality at about 24 hours after exposure) were obtained with the kaolin control formulation at a dosage level of 47 µg/cm². A high percentage of control (distilled water only treated) houseflies from the USDA ARS Gainesville colony did not survive at 24 hours (Table 3), so comparisons could not be made from this data set.

Figure 3:
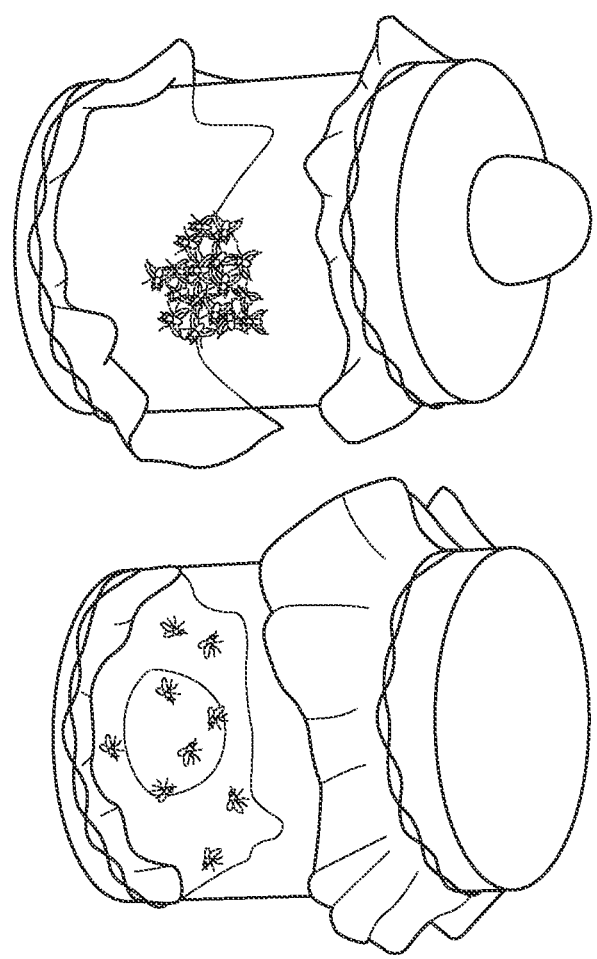
FIG. 3 is a photograph of results after housefly cylinder spray tests with a composition according to FIG. 1 with right hand side, showing all of houseflies knocked down compared to a distilled water control, left hand side, showing the unaffected houseflies.
Figure 5:
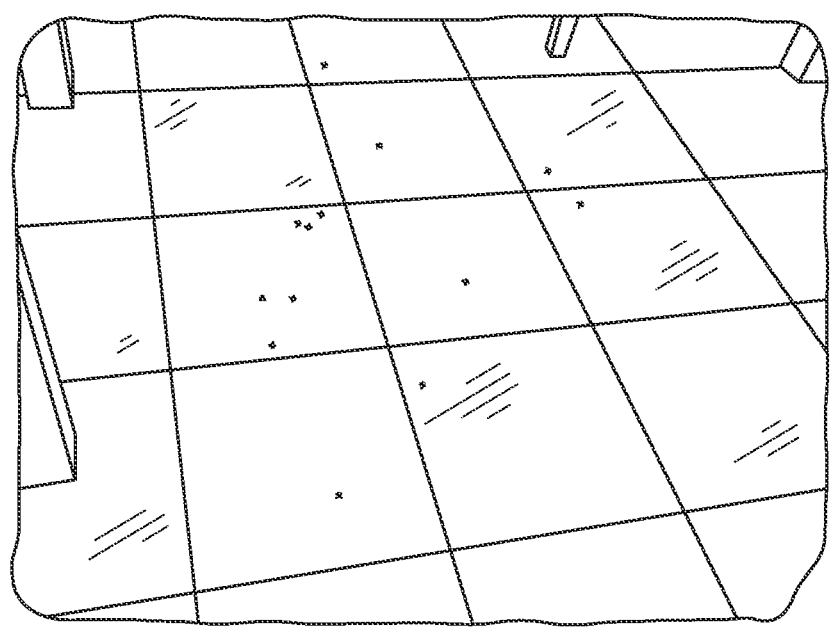
FIG. 5 is a photograph of results after a housefly room spray test with a composition accordingly to FIG. 1.

Cylinder spray tests of a 1/10 dilution of the aqueous slurry concentrate (having about 2.7% of the arthropod actives) against houseflies (Table 9) was highly effective showing immediate and complete incapacitation of about 100%, and complete morality of about 100% at about 24 hour after exposure. FIG. 3 shows the housefly cylinder spray tests with a 1/10 dilution of the aqueous slurry concentration on the right hand side of the figure with all of the flies knocked down and the distilled water spray control on the left hand side with the unaffected houseflies. Furthermore, a room spray test of a 1/10 dilution of the aqueous slurry concentrate (Table 15) was highly effective against houseflies. FIG. 5 shows housefly room spray tests with a 1/10 dilution of the aqueous concentrate showing the down houseflies that were swept under the table.

German Cockroaches

German cockroaches were somewhat less sensitive than houseflies. The cockroaches showed lower levels of incapacitation and mortality at a dosage level of about 431 µg/cm² (1/10 dilution, Table 4). In the free choice cage tests (Tables 5-7), cockroach incapacitation was low (≤40%) with the aqueous slurry concentrate and with the 1/10 dilution, as compared to the kaolin control applied as a powder or as an aqueous dispersion.

Spray tests against German cockroaches showed that they may be resistant to the effects of encapsulated arthropod active agent (Tables 11-14). However, the male cockroaches may be more sensitive than females to the encapsulated arthropod active agent. FIGS. 4A and 4B show the German cockroach cylinder spray tests (on the left hand side) with a 1/10 dilution of the aqueous slurry concentration with all of the German cockroach knocked down. By way of example only, a kaolin control having about 15 wt % of $C_8$, $C_9$ and $C_{10}$ fatty acids in a water dispersion at about a 0.3 wt % fatty acid actives level resulted in 100% immediate incapacitation and 100% mortality at 24 hours.

Argentine Ants

Figure 6A:
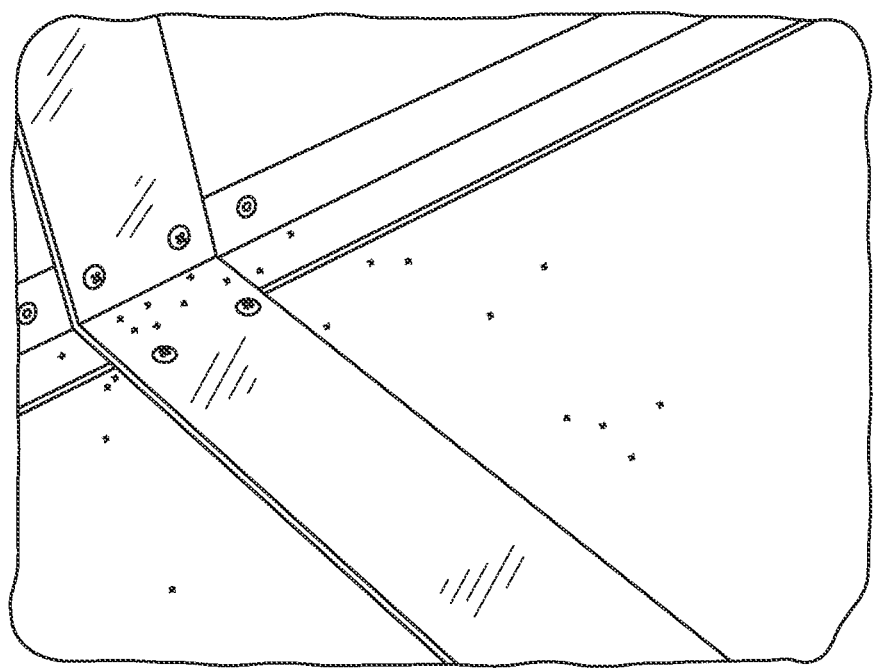
FIGS. 6A and 6B are photographs showing the residual effect of a composition according FIG. 1 on Argentine ants.
Figure 6B:
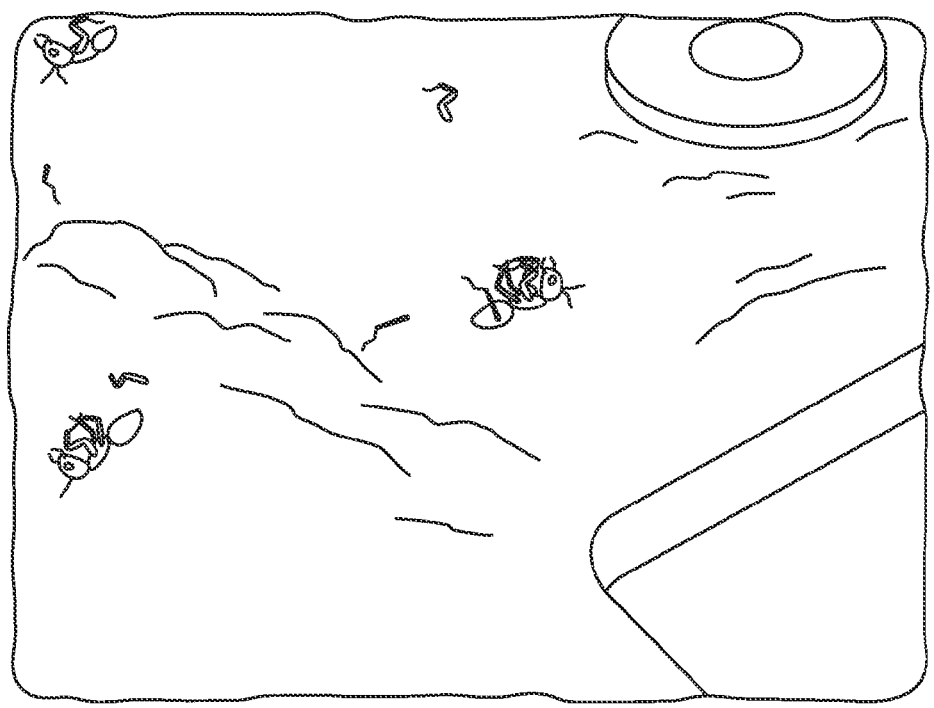
Figure 7:
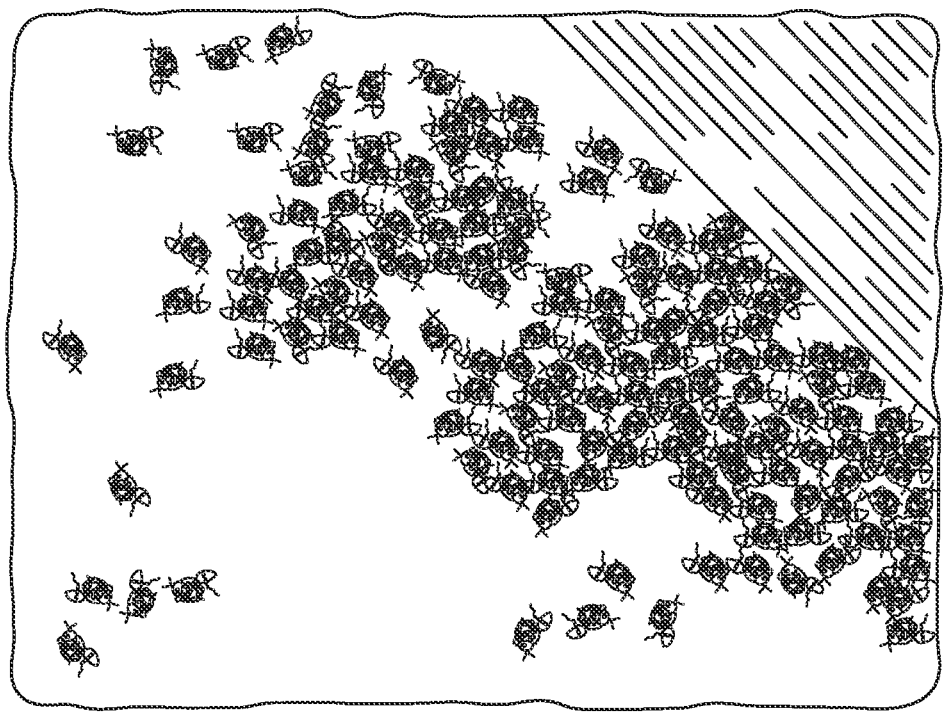
FIG. 7 is a photograph of Argentine ants killed by a composition according to the prior art.

Directly spraying a dilute formulation of the aqueous slurry composition on Argentine ants caused immediate incapacitation (FIGS. 6A and 6B). Furthermore, the dilute formulation appeared to have a residual effect. After removing the ants killed by the direct spraying, new dead ants appeared in the area where the dilute formulation had been applied. The kaolin control formulation can also kill Argentine ants (FIG. 7).

Thermogravimetric Analysis

Figure 8A:
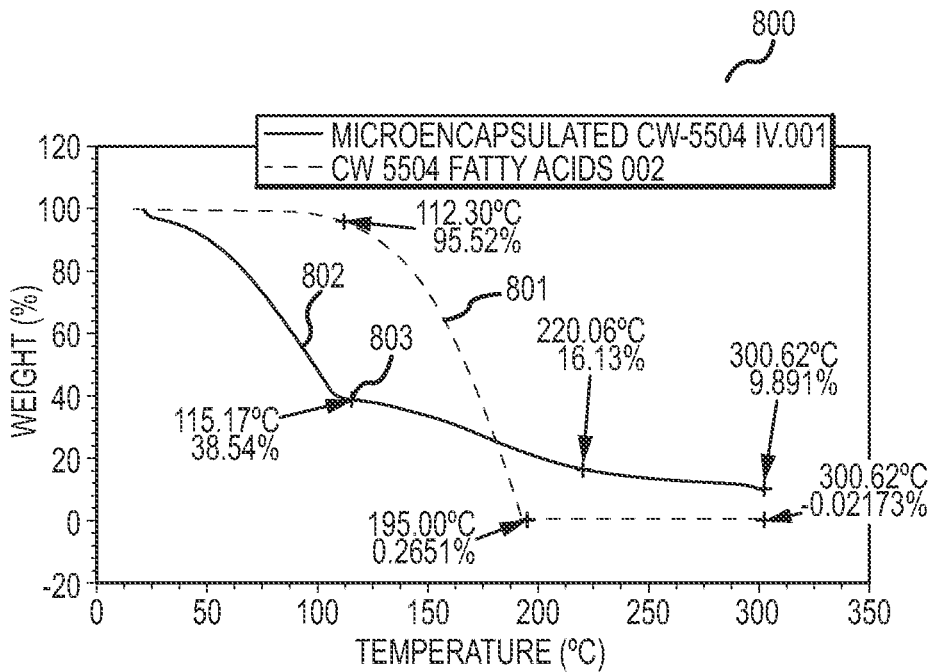
FIGS. 8A and 8B are thermograms comparing a composition according to FIG. 1 and an unencapsulated control.
Figure 8B:
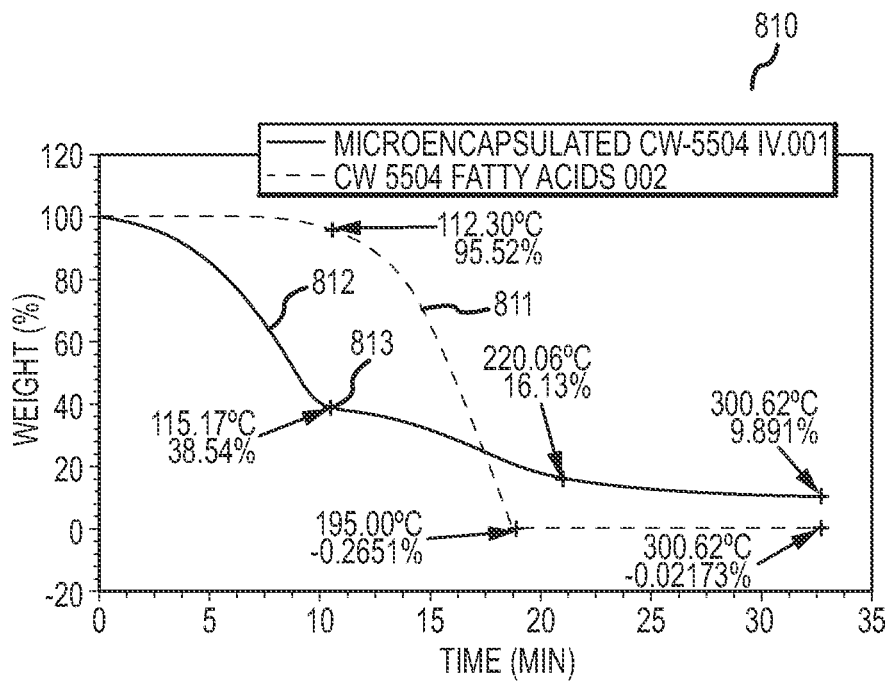

FIGS. 8A and 8B shows the effect of encapsulation on fatty acid release rate. The dynamic flowing air thermogravimetric analysis was conducted on encapsulated and free CW5504 fatty acid comprising equal parts of octanoic, nonanoic and decanoic acids. Thermograms were ran by ramping to 300 degrees Celsius at 10 degrees Celsius/min and held for 5 minutes. The thermograms 800 and 810 are displayed, respectively, in temperature and time domains. An analysis of the microencapsulated thermograms 802 and 812 show loss of water and small amounts of fatty acid up to temperatures of about 110 degrees Celsius, see points 803 and 813. At temperatures above about 110 degrees Celsius, the fatty acid is lost at a slower rate in the encapsulated material (thermograms 802 and 812) than in the free, unencapsulated material (thermograms 801 and 811)

A number of variations and modifications of this disclosure can be used. It would be possible to provide for some features of this disclosure without providing others.

The present disclosure, in various embodiments, configurations, or aspects, includes components, methods, processes, systems and/or apparatus substantially as depicted and described herein, including various embodiments, configurations, aspects, sub-combinations, and subsets thereof. Those of skill in the art after reading this disclosure will understand how to make and use the subject matter of this disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the subject matter of the disclosure to the form or forms disclosed herein. In the foregoing Detailed Description for example, various features are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention that the claimed subject matter requires more features than are expressly recited in each claim. Rather, as the following claims reflect, claimed aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, the description has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A composition, comprising:
   a wall defining a void volume, wherein the wall comprises a polymeric material; and
   an active arthropod agent filling at least most of the void volume, wherein the wall is permeable to and releases the active arthropod agent and wherein the active arthropod agent comprises a fatty acid having six or more carbon atoms or a mixture thereof.

2. The composition of claim 1, wherein the active arthropod agent has a calculated vapor pressure at 25 degrees Celsius of more than about $1\times10^{-6}$ mm Hg, wherein the polymeric material releases the arthropod agent at a rate at about 32 degrees Celsius from about 0.02 to about 19 μg/cm$^2$-h, and wherein the composition is in the form of capsules having an average capsule size of no more than about 1,000 μm.

3. The composition of claim 1, wherein the active arthropod agent comprises one or more of a $C_8$ fatty acid, $C_9$ fatty acid, and $C_{10}$ fatty acid.

4. The composition of claim 1, wherein the active arthropod agent comprises one or more of a $C_6$ fatty acid, $C_7$ fatty acid, $C_8$ fatty acid, $C_9$ fatty acid, and $C_{10}$ fatty acid.

5. The composition of claim 1, wherein the polymeric material comprises one of a polyurethane, polyurea, urea-formaldehyde, urea-resorcinol-formaldehyde, melamine formaldehyde or combination thereof.

6. The composition of claim 1, wherein the polymeric material comprises melamine formaldehyde.

7. The composition of claim 1, wherein the wall defines a capsule having a capsule size from about 1 to about 100 μm.

8. The composition of claim 1, wherein the active arthropod agent fills more than about 90% of the void volume.

9. A device, comprising:

a plurality of capsules, wherein each of the capsules comprising the plurality of capsules comprises a wall defining a void volume and an active arthropod agent filing most of the void volume, wherein the wall is permeable to and releases the active arthropod agent, wherein the wall comprises a polymeric material, and wherein the active arthropod agent comprises a fatty acid having six to ten carbon atoms and wherein the capsules have an average capsule size.

10. The device of claim 9, wherein the active arthropod agent has a calculated vapor pressure at 25 degrees Celsius of more than about $1\times10^{-6}$ mm Hg, wherein the polymeric material releases the arthropod agent at a rate at about 32 degrees Celsius from about 0.05 to about 18 μg/cm$^2$-h, and wherein the average capsule size is no more than about 1,000 μm.

11. The device of claim 9, further comprising:

discrete gel droplets of a cross-linked gel comprising a gelling agent and a cross-linking agent, wherein the discrete gel droplets are in the form of one of a continuous or discontinuous film, and wherein the discrete gel droplets interconnect the plurality of capsules.

12. The device of claim 11, wherein the gelling agent comprises one of a polysaccharide, nonionic polymer, inorganic polymer, polyanion, polycation, alginate, natural ionic polysaccharide, chitosan, gellan gum, xanthan gum, hyaluronic acid, heparin, pectin, carrageenan, polyacrylic acid, polymethacrylic acid, a polyethylene imine, polylysine, polyvinyl alcohol, sodium silicates, and mixtures thereof, and wherein the cross-linking agent comprises a multivalent ion.

13. The device of claim 12, wherein the multivalent ion comprises one of magnesium, calcium, zinc, barium, strontium, aluminum, iron, manganese, nickel, cobalt, copper, cadmium, lead, or mixtures thereof.

14. The device of claim 9, wherein the polymeric material comprises one of a polyurethane, polyurea, urea-formaldehyde, urea-resorcinol-formaldehyde, melamine formaldehyde or combination thereof, wherein the plurality of capsules have an average capsule size from about 1 to about 100 μm, and wherein the active arthropod agent comprises one of:

i) one or more of a $C_6$ fatty acid, $C_7$ fatty acid, $C_8$ fatty acid, $C_9$ fatty acid, and $C_{10}$ fatty acid; or ii) one or more of a $C_8$ fatty acid, $C_9$ fatty acid and $C_{10}$ fatty acid.

15. The device of claim 9, further comprising:

a target substrate, wherein the target substrate comprises one of a fluid, hard surface, polymeric coating, botanical organism, foodstuff, textile, or an animal raised for profit.

16. A system, comprising:

one or more capsules, each of the capsules having:

a wall defining a void volume;

an active arthropod agent filling most of the void volume, wherein the wall is a polymeric material that one or both controls release rate and period of efficacy of the active arthropod agent and wherein the active arthropod agent comprises a fatty acid having six or more carbon atoms; and an active arthropod agent release rate at about 32 degrees Celsius of more than about 22 μg/cm$^2$-h, wherein the active arthropod agent is released by the polymeric material.

17. The system of claim 16, wherein the active arthropod agent has a calculated vapor pressure at 25 degrees Celsius of more than about $1\times10^{-6}$ mm Hg, wherein the polymeric material controls one or both of:
  i) the rate of release of the active arthropod agent into the environment, wherein the wall decreases the rate of release of the active arthropod agent into the environment by 90% or less compared to non-encapsulated active arthropod agent; and
  ii) the period of efficacy of the active arthropod agent, wherein the wall increases the period of efficacy of the active arthropod agent contained within the capsules by more than about 110% compared to the same active arthropod agent not contained within the capsules.

18. The system of claim 16, further comprising:
a target substrate, wherein the one or more capsules are positioned one or both of on or in the target substrate, wherein the target substrate comprises one of a fluid, hard surface, polymeric coating, botanical organism, foodstuff, textile, or an animal raised for profit.

19. The system of claim 18, further comprising:
discrete gel droplets of a cross-linked gel comprising a gelling agent and a cross-linking agent, wherein the discrete gel droplets:
interconnect the one or more capsules to the target substrate; and
are in the form of one of a continuous or discontinuous film.

20. The system of claim 19, wherein the gelling agent comprises one of a polysaccharide, nonionic polymer, inorganic polymer, polyanion, polycation, alginate, natural ionic polysaccharide, chitosan, gellan gum, xanthan gum, hyaluronic acid, heparin, pectin, carrageenan, polyacrylic acid, polymethacrylic acid, a polyethylene imine, polylysine, polyvinyl alcohol, sodium silicates, and mixtures thereof, and wherein the cross-linking agent comprises one of magnesium, calcium, zinc, barium, strontium, aluminum, iron, manganese, nickel, cobalt, copper, cadmium, lead, or mixtures thereof.

21. The system of claim 16, wherein the one or more capsules have an average capsule size of no more than about 1,000 μm.

22. The system of claim 16, wherein the polymeric material comprises one of a polyurethane, polyurea, urea-formaldehyde, urea-resorcinol-formaldehyde, melamine formaldehyde or combination thereof, wherein the one or more capsules have an average capsule size from about 1 to about 100 μm, and wherein the active arthropod agent comprises one of:
  i) one or more of a $C_6$ fatty acid, $C_7$ fatty acid, $C_8$ fatty acid, $C_9$ fatty acid, and $C_{10}$ fatty acid; or
  ii) one or more of a $C_8$ fatty acid, $C_9$ fatty acid, and $C_{10}$ fatty acid.

23. The system of claim 16,
wherein the release rate of the active arthropod agent is sufficient to one or more of repel, impair, incapacitate or kill an arthropod.

* * * * *